United States Patent [19]

Yost et al.

[11] Patent Number: 5,247,251
[45] Date of Patent: Sep. 21, 1993

[54] PROBE WITH RADIALLY EXTENDABLE AND RETRACTABLE DETECTOR ASSEMBLY FOR INSPECTING INTERIOR WALLS OF HOLLOW METALLIC PLUG

[75] Inventors: William D. Yost, West Mifflin; Randall A. Holmes, Delmont; Michael D. Coradi, Wilkinsburg; Andrew J. Frank, Jr., Richeyville, all of Pa.

[73] Assignee: Westinghouse Electric Corp., Pittsburgh, Pa.

[21] Appl. No.: 852,444

[22] Filed: Mar. 16, 1992

[51] Int. Cl.$^5$ .............. G01N 27/90; G21C 17/017
[52] U.S. Cl. .................. 324/220; 33/544.3; 165/11.1; 376/245
[58] Field of Search .............. 324/219–221; 33/542, 543, 544.2, 544.3; 165/11.1, 11.2; 376/245

[56] References Cited

U.S. PATENT DOCUMENTS

| | | | |
|---|---|---|---|
| 4,105,972 | 8/1978 | Smith | 324/220 |
| 4,341,113 | 7/1982 | Gutzwiller, Jr. | 73/105 |
| 4,625,165 | 11/1986 | Rothstein | 324/220 |
| 4,851,773 | 7/1989 | Rothstein | 324/220 |
| 4,937,524 | 6/1990 | Fasnacht et al. | 324/220 |
| 4,992,735 | 2/1991 | Cullen et al. | 324/220 |
| 5,134,367 | 7/1992 | Griffith et al. | 324/220 |

*Primary Examiner*—Gerard R. Strecker
*Attorney, Agent, or Firm*—W. S. Stevens

[57] ABSTRACT

An eddy current probe, especially useful for inspecting roll plugs in steam generator tubes, has a detector assembly which is automatically extended and retracted in a radial recess in an elongated body to prevent damage to the detector assembly during insertion and retraction of the probe, yet permits the detector assembly to bear against the interior wall of the roll plug, including the roll zone. In one embodiment, a mechanical actuator in the form of a pair of finger members spring biased radially outward operate through camming surfaces to rotate a pivot member which retracts the detector assembly; however, when the probe enters the bore of a roll plug the fingers are compressed to permit extension of the detector assembly. In another embodiment, a linear actuator such as a solenoid rotates the pivot member to extend and retract the detector assembly. A lost motion connection between the pivot member and the spring biased eddy current detector assembly permits the detector assembly to track the interior surface of the roll plug including the roll zone.

21 Claims, 3 Drawing Sheets

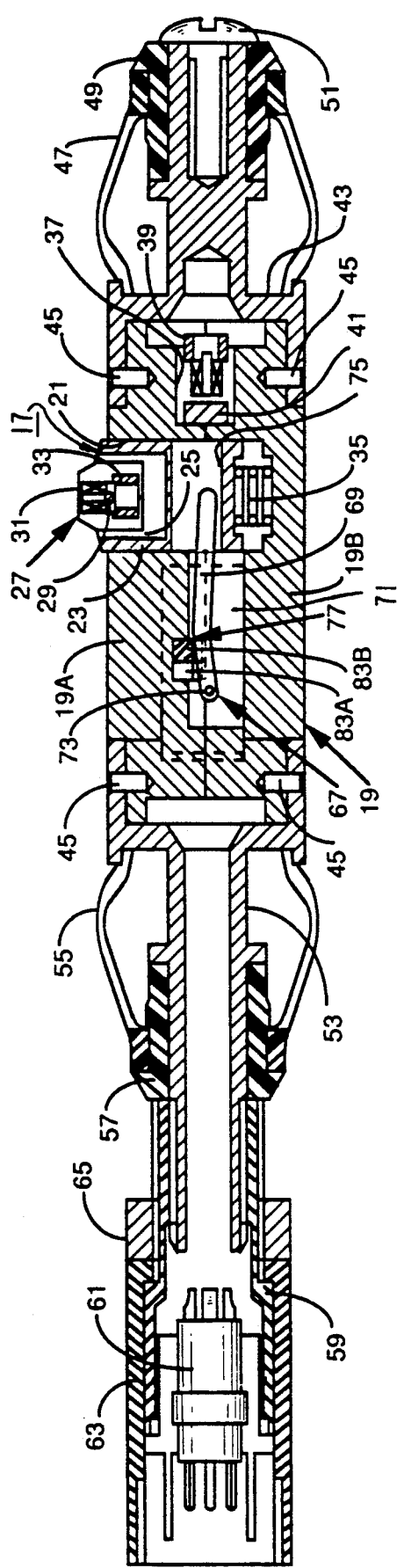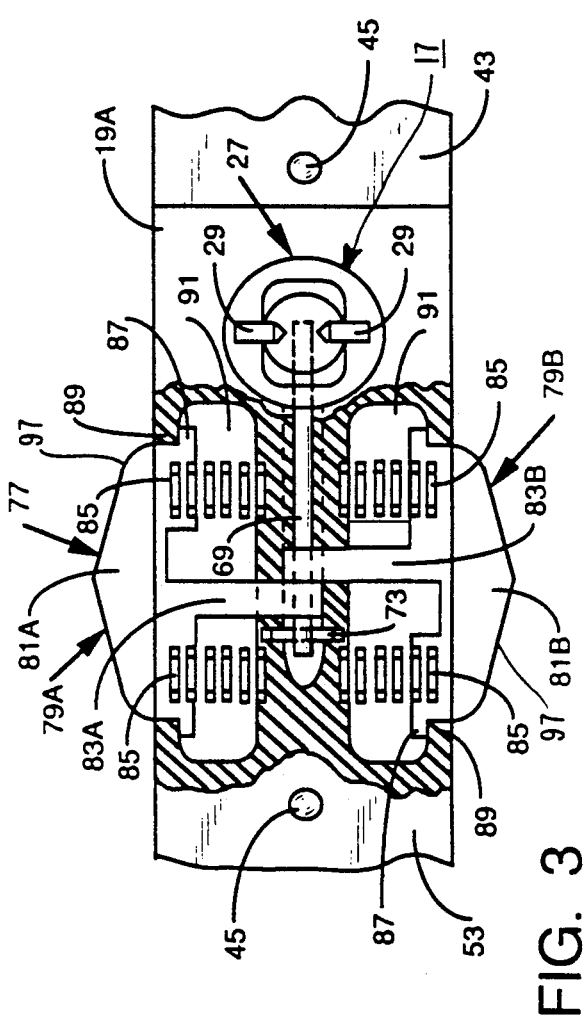

PROBE WITH RADIALLY EXTENDABLE AND RETRACTABLE DETECTOR ASSEMBLY FOR INSPECTING INTERIOR WALLS OF HOLLOW METALLIC PLUG

BACKGROUND OF THE INVENTION

1. Field of the Invention

This invention is directed to probes for inspecting the interior walls of cavities in electrically conductive objects, more particularly to inspecting the interior walls of hollow metallic plugs inserted in the tubes of heat exchangers and having a cylindrical bore with a radially expanded section and a narrower opening. Specifically, it is directed to a probe with a radially extendable and retractable eddy current detector assembly.

2. Background Information

Eddy current detectors, known in the art, are used to inspect the tubes of heat exchangers, and in particular, the tubes of nuclear steam generators. The eddy current detector consists of a pancake-style eddy current coil mounted in an inspection probe. The probe is inserted into a steam generator tube at the tube sheet, and gradually moved upward while being rotated inside the tube, thus inspecting the integrity of the tube in a helical pattern. The pancake coil is typically mounted in a spring-loaded housing which is designed to allow the pancake coil to extend and swivel slightly to remain in contact with the tube wall in out-of-round sections or other none-uniform areas.

In addition to inspecting tubes, it has become necessary to inspect "roll plugs" installed in out-of-service tubes to ensure the integrity of the plug. Roll plugs are secured in the out of service tube by radially expanding a section of the bore in the plug. This creates a "roll zone" which is somewhat larger in diameter than the remainder of the bore in the plug. This roll zone is spaced from the opening in the roll plug. Consequently, the eddy current detector used to inspect the roll plug must be mounted in the housing which extends the detector into this larger-diameter area to maintain contact with the walls in the roll zone. A previous type of probe incorporated an eddy current detector which was simply spring-loaded, thereby insuring that the detector would extend to the plug wall in the roll zone. However, this probe was sometimes destroyed upon an insertion into a roll plug when the extended spring loaded detector housing caught at the opening and was torn out of the probe. An example of an eddy current detector which is merely spring biased outward from a probe is disclosed in U.S. Pat. No. 4,625,165. U.S. Pat. No. 4,992,735 discloses a probe with an eddy current detector mounted on the end of a leaf spring which is retracted axially into a probe housing to protect the detector while the probe is maneuvered past a retainer ring in the plug. This device requires a special, sizable end effector for a robot which performs the inspection.

There remains a need for an improved eddy current detector probe for inspecting cavities in electrically conductive objects with narrowed openings, and in particular for inspecting roll plugs for steam generator tubes.

There is a further need for such an improved probe which retracts the eddy current detector within the probe body for insertion and retraction of the probe, yet biases the detector against the surface of the object to be inspected when in use.

There is a preferred need for a probe which automatically extends and retracts the eddy current detector to eliminate operator error in failing to retract the probe.

There is also a need for providing improved probes as described above which can be used with standard eddy current inspection systems and with minimum requirements for modifications to the inspection system.

SUMMARY OF THE INVENTION

The objects of the invention are to satisfy the above needs and others. This is accomplished by a probe which has a radial recess in which an eddy current detector assembly is slidable, and actuating means for selectively extending the eddy current detector assembly radially outward from the radially extending recess against the wall of the cavity in the object to be inspected with the elongated body inserted into the cavity, and retracting the eddy current detector assembly radially inward within the recess for inserting and removing the elongated body through the narrowed opening in the cavity.

In accordance with one embodiment of the invention, mechanical means maintain the eddy current detector assembly retracted within the radial recess in the probe and automatically extend the detector into contact with the wall of the cavity, such as the bore in a roll plug, automatically upon insertion of the probe into the opening. This mechanical means includes a pair of fingers biased radially outward, and coupling means coupling the mechanical fingers to the eddy current detector assembly so that with the fingers extended, the detector is retracted and when the fingers are depressed by insertion into the opening in the roll tube, the detector is extended. The coupling includes a pivot member engaged by the fingers, and through a lost motion connection, by the eddy current detector assembly. A spring biases the eddy current detector assembly radially outward against the plug wall, but a stronger spring biases the fingers radially outward to maintain the detector in the retracted position.

The coupling between the finger members and the eddy current detector assembly includes a pivot member pivoted about a pivot axis transverse to the radial recess in the elongated body. The lost motion connection is implemented by one end of the pivot member which engages a slot in the carrier of the eddy current detector assembly. The pivot member is also engaged by inclined camming surfaces on stems of the finger members which form a V which wedges against the pivot member to rotate it when shoes on the finger members are pressed inward by contact with the opening in the roll tube. Both finger members must be depressed simultaneously to extend the eddy current detector assembly.

In another embodiment of the invention, the pivot member is actuated by a linear actuator such as a solenoid. With the solenoid deenergized, the eddy current detector assembly is retracted. The solenoid can be wired to be energized with the rotating probe head so that the eddy current detector is automatically extended when the head begins to turn after insertion into the roll tube.

BRIEF DESCRIPTION OF THE DRAWINGS

A full understanding of the invention can be gained from the following description of the preferred embodiments when read in conjunction with the accompanying drawings in which:

FIG. 2 is a longitudinal sectional view through the probe of FIG. 1.

FIG. 3 is a fragmentary side view with parts broken away of the probe of FIGS. 1 and 2.

DESCRIPTION OF THE PREFERRED EMBODIMENTS

Figure 1:
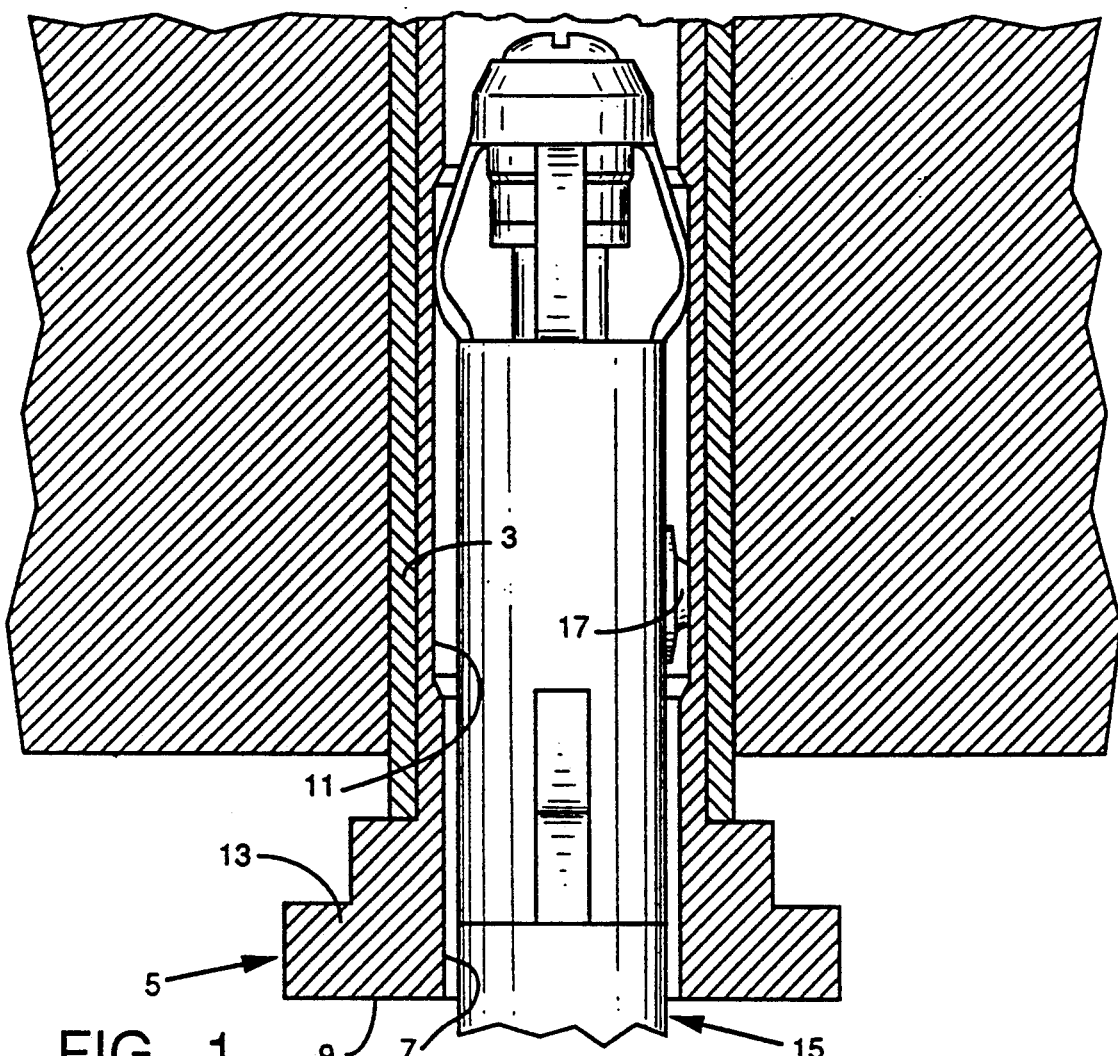
FIG. 1 is a vertical section through the tube sheet of a nuclear steam generator showing a probe in accordance with the invention in place to perform an inspection on a roll plug.

The present invention is especially useful in inspecting roll plugs installed in the tubes of a nuclear steam generator. FIG. 1 illustrates a cross-section through a portion of the tube sheet 1 of a nuclear stream generator. Thousands of heat exchanger tubes 3 are secured in bores through the tube sheet 1. At times it is necessary to plug tubes for various operational reasons. This is accomplished by inserting a plug 5 into the end of the tube 3 to be sealed off. The plug has a blind cylindrical bore 7 forming a cavity with an open end 9. The roll plug is secured in the tube 3 by expanding radially outward a portion of the plug wall to form a roll zone 11 which is greater in diameter than the remainder of the bore 7. The roll plug has a stepped flange 13 at the open end 9 for engagement by an end effector (not shown) which installs the plug.

Periodically, the roll plugs 5 are inspected to insure plug integrity. Testing is typically conducted with an eddy current probe. FIG. 1 illustrates a probe 15 in accordance with a first embodiment of the invention inserted into the bore 5 for performing such an inspection. The probe 15 includes an eddy current detector assembly 17 which must be in contact with the wall of the plug 5 in order to generate accurate readings. However, as can be seen from FIG. 1, the opening 9 in the roll plug is narrower than the roll zone 11. In accordance with the invention, the eddy current detector assembly 17 is biased outward to maintain contact with the wall of the bore in the roll plug including the, roll zone; however, it is retracted for insertion and removal of the probe to prevent damage.

Turning to FIGS. 2 and 3, the probe 15 has an elongated body 19 formed of two body halves 19a and 19b. The elongated body 19 has a radially extending recess 21 in which the eddy current detector assembly 17 is radially slidable. The eddy current detector assembly includes a housing 23 with a radial bore 25 in which the detector unit 27 is pivotally mounted by pins 29. The detector unit 27 includes a pancake-type eddy current coil 31 and a bias magnet 33 encased in ultra high molecular weight polyethylene. The housing 23, and hence the detector unit 27, is biased radially outward in the recess 21 by a helical compression spring 35.

The elongated body 19 has a longitudinal bore 37 in the distal end in which a reference detector unit 39 and a target 41 are mounted. A cylindrical front shaft piece 43 clamps the elongated body halves 19a and 19b together and is secured in place by a pair of roll pins 45.

A multi-petal resilient centering head 47 is mounted on the end of the front shaft 43 by a bushing 49 which in turn is held in place by a round head screw 51 threaded into the end of the front shaft 43.

A rear shaft 53 clamps the proximal ends of the body halves 19a and 19b and is also held in place by roll pins 45. A rear centering head 55 with multiple resilient petals is mounted on the rear shaft 53 by a bushing 57. A tubular housing 59 threaded onto the rear shaft 53 contains a male connector 61. Wires (not shown) lead from the male connector 61 through the rear shaft 53 and through passages (not shown) in the elongated body 19 to detector units 27 and 39. A C-nut 63 connects the probe to a probe lead (not shown) which provides electrical power to the detector units through the male connector 61, and which rotates the probe as it is fed into the tube plug so that the pancake coil scans the entire surface of the bore in the roll plug in a helical scanning pattern.

The eddy current detector assembly 17 is reciprocally extended and retracted in the radial recess 21 by an actuator 67. This actuator 67 includes a pivot member in the form of the rod 69 which is mounted in a chamber 71 in the elongated body 19 by a pin 73 for rotation about a pivot axis transverse to the direction of movement of the eddy current assembly 17 in the radial recess 21. The free end of the pivot rod 69 engages the eddy current detector assembly 17 through a lost motion connection formed by a slot 75 in the housing 23 of the eddy current detector assembly which is wider than the free end of the rod.

Figure 4:
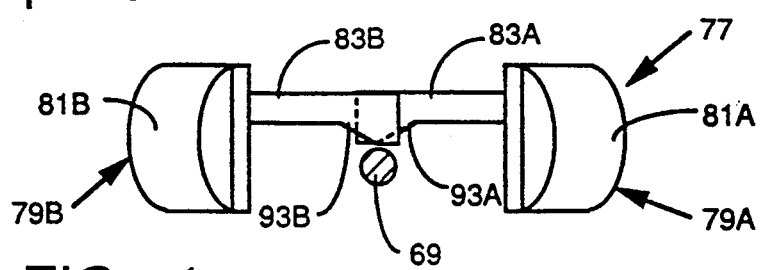
FIG. 4 is a schematic view of finger members of the probe of FIGS. 1-3 shown in a normal, eddy current detector assembly stowed position.
Figure 5:
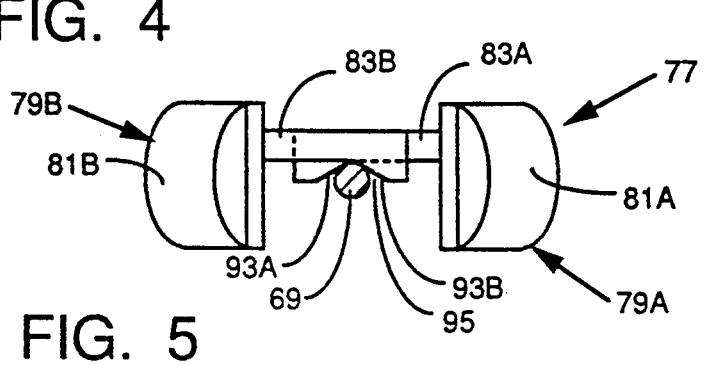
FIG. 5 is a schematic view of the finger members of FIG. 4 shown in the actuated, eddy current detector assembly operating position.

The rod 69 is pivoted by a mechanical actuator 77 which includes a pair of diametrically opposed finger members 79A and 79B. The finger members 79A and 79B have outwardly directed shoes 81A and 81B and parallel adjacent stems 83A and 83B which overlap. The finger members 79A and 79B are biased radially outward by pairs of helical compression springs 85. Lips 87 on the shoes 81A and 81B engage shoulders on the recesses 91 in the elongated body 19 in which the finger members are mounted to limit extension of the shoes 81A and 81B. As best seen in FIGS. 4 and 5, the stems 83A and 83B have opposed inclined camming surfaces 93 which form a V-shaped groove 95 in which the pivoted rod 69 is seated. With the finger members 79A and 79B extended outward by the springs 85, the inclined surfaces 93 on the stems 83A and 83B are drawn in opposite directions to reduce the size of the V-shaped groove 95 which rotates the pivoted rod 69 in the clockwise direction as shown in FIG. 2. This clockwise rotation of the rod 69 results in retraction of the eddy current detector assembly 17 in the radial recess 21 as the four springs 85 are collectively stronger than the spring 35. Thus, with the finger members extended radially outward, the eddy current detector assembly 17 is retracted into the radial recess 21.

The outer surface 97 of the shoes 81A and 81B is tapered in both axial directions to form camming surfaces which engage the bore of the roll plug to be inspected. It will be noticed that the radial recess 21 housing the eddy current detector assembly 17 is positioned between the distal end of the probe and the finger members 79A and 79B so that the eddy current detector assembly remains retracted as the probe is inserted into the roll plug to prevent damage thereto. The detector assembly remains retracted until the probe is inserted sufficiently that the shoes 81A and 81B, which extend radially outward to a greater diameter than the bore in the roll plug, begin to enter the roll plug and are compressed thereby. As the finger members are compressed, camming surfaces 93 slide relative to one another to increase the size of the V-shaped groove 95. This permits the pivoted rod 69 to rotate counterclockwise, as seen in FIG. 2, as the spring 35 urges the eddy current detector assembly 17 radially outward in the recess 21. The lost motion connection formed by the free end of the rod 69 and the slot 75 in the housing 23 is dimensioned such that the spring 35 can maintain the eddy current detector assembly 17 in contact with the interior wall of the roll plug even in the roll zone 11. Upon retraction of the probe 15, the finger members 79A and 79B the opening 9 in the plug and are extended radially by the springs 85 to retract the eddy current detector assembly 17 before it emerges from the bore of the roll plug. It should be noticed that finger members 79A and 79B must be compressed simultaneously in order to extend the eddy current detector assembly 17.

Figure 6:
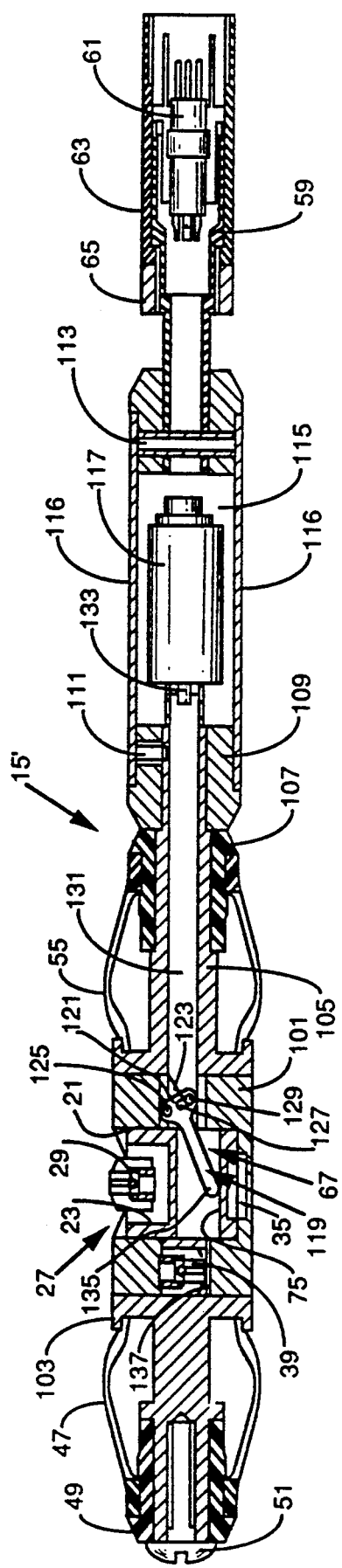
FIG. 6 is a longitudinal sectional view through a probe in accordance with another embodiment of the invention.

FIG. 6 illustrates another embodiment of the invention. Like parts with the embodiment of FIGS. 1-5 are identified with the same reference characters. This probe 15' includes the eddy current detector assembly 27 spring biased outward by a compression spring 35 in a radial recess 21 in a cylindrical elongated body 101. A front shaft 103 integral with the body 101 supports a multi-petal resilient centering head 47 mounted on the end of the front shaft 103 by a bushing 49 which in turn is held in place by a round head screw 51 threaded into the end of the front shaft 103.

A rear shaft 105, which is also integral with the elongated body 101, supports a multi-petal rear centering head 55 through bushing 107. A solenoid housing 109 is secured to the rear shaft 105 by set screws 111 (only one shown). The other end of the housing 109 is secured to the tubular housing 59 by a roll pin 113.

The solenoid housing 109 has a cavity 115 enclosed by covers 116 in which a solenoid 117 is mounted. While not shown in FIG. 6, the electrical leads for the solenoid 117 extend through the tubular housing 59 to the male connector 61. As in the case of the first described embodiment of the invention, the eddy current detector assembly 27 is reciprocally extended and retracted in the radial recess 21 by an actuator 67. In this embodiment of the invention, the actuator 67 includes a pivot member in the form of a T-shaped bell crank 119. The one end of the cross bar 121 of the bell crank 119 is mounted in a chamber 123 in the elongated body 101 by a pin 125 for rotation about a pivot axis transverse to the direction of movement of the eddy current assembly 27 in the radial recess 21. The other end of the cross bar 121 has a slot 127 through which the bell crank 119 is connected by a pin 129 to the bifurcated tapered end of a tubular push rod 131 which reciprocates in the bore of the rear shaft 105. The tubular push rod 131 is reciprocated by a linear actuator in the form of the solenoid 117 which has its actuating rod 133 connected to the tubular push rod 131. While a solenoid is preferred as the linear actuator, other devices such as, for instance, pneumatic or hydraulic actuators could also be used. The stem 135 of the bell crank 119 engages the slot 75 to form a lost motion connection between the bell crank and the eddy current detector assembly 27.

With the solenoid 117 deenergized, the tubular push rod 131 is retracted to rotate the bell crank 119 counterclockwise, as viewed in FIG. 6, to retract the eddy current detector assembly 27 against the bias force generated by the spring 35. When the solenoid 117 is energized, the actuating rod 133 is extended to push the tubular push rod 131 to the left as seen in FIG. 6 and rotate the bell crank 119 clockwise so that the spring 35 can bias the eddy current detector assembly 27 outward against the inner wall of the steam generator tube or plug to perform the inspection. As in the case of the previously described probe 15, the probe 15' includes a reference detector assembly 39 mounted in a bore 137 in the forward end of the housing 101. Preferably, the solenoid 117 is wired for energization with the motor (not shown) which rotates the probe once the probe is inserted in the steam generator tube roll plug, so that the eddy current detector assembly remains retracted for insertion but is automatically extended when the inspection process is initiated with the probe in place inside the tube or plug. As the motor drive is deenergized to stop rotation of the probe before withdrawal from the tube plug, the eddy current detector assembly is automatically retracted to protect it from damage as the probe is withdrawn.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A probe for inspecting the interior walls of the cavity within an electrically conductive object, even when said cavity has an opening narrower in width than said cavity, said probe comprising:

an elongated body insertable into aid cavity through said opening and having a radially extending recess;

an eddy current detector assembly slidable radially in said radially extending recess in said elongated body; and actuating means engaging said eddy current detector assembly for selectively extending said eddy current detector assembly radially outward from said radially extending recess against the interior walls of said cavity with said elongated body inserted into said cavity and retracting said eddy current detector assembly radially inward within said recess during insertion into and removal of said elongated body from said cavity through said opening.

2. The probe of claim 1 wherein said actuating means comprises means automatically extending said eddy current detector assembly with said radially extending recess inside said cavity and automatically retracting said eddy current detector assembly before the radially extending recess leaves said cavity as said elongated body is removed from said cavity.

3. The probe of claim 1 wherein said actuating means includes a pivot member pivoted for rotation about a pivot axis transverse to said radially extending recess, and an actuator selectively reciprocally rotating said pivot member about said pivot axis, said pivot member engaging said eddy current detector assembly to extend and retract said eddy current detector assembly as said pivot member is rotated by said actuator.

4. The probe of claim 3 wherein said actuating means includes biasing spring means biasing said eddy current detector assembly radially outward against said interior wall of said cavity and wherein said pivot member engages said eddy current detector assembly through a lost motion coupling.

5. The probe of claim 4 wherein said eddy current detector assembly comprises a housing slidable in said radially extending recess and an eddy current coil mounted on said housing, and wherein said lost motion coupling comprises a slot in said housing wider than said pivot member.

6. The probe of claim 5 wherein said actuator comprises a solenoid.

7. The probe of claim 5 wherein said actuator comprises finger members radially extendable and retractable from said elongated body and engaging said pivot member to pivot said pivot member to retract said eddy current detector assembly when said fingers are extended and to extend said eddy current detector assembly when said fingers are retracted, second spring means stronger than said biasing spring extending said finger members, and therefore retracting said eddy current detector assembly, said finger members being mounted in said elongated body member in spaced relation to said radially extending recess such that said eddy current detector assembly is within said cavity when the finger members enter said opening and are retracted by engagement with walls of the cavity to extend said eddy current detector assembly against the walls of said cavity.

8. A probe for inspecting the interior walls of a hollow metallic plug having an open end and a cylindrical bore with a radially expanded section spaced from said open end, said probe comprising:
an elongated body insertable into said cylindrical bore through said open end, and having a radially extending recess;
an eddy current detector assembly slidable radially in said radially extending recess; and
mechanical actuator means retracting said eddy current detector assembly within said radially extending recess in said elongated body and extending said eddy current detector assembly from said radially extending recess into contact with said cylindrical bore upon insertion of said probe into said cylindrical bore and contact of said bore by said mechanical actuator means.

9. The probe of claim 8 wherein said mechanical actuator means comprises finger members generally radially extendable and retractable from said elongated body member, coupling means coupling said finger members to said eddy current detector assembly for extending said eddy current detector assembly when said finger members are in a retracted position and retracting said eddy current detector assembly into said radially extending recess when said finger members are in an extended position, and biasing means biasing said finger members to said extended position, said radially extending recess being positioned on said elongated body between a free end of said elongated body and said finger members, so that said eddy current detector assembly remains retracted in said radially extending recess as said free end of said elongated body is inserted into said cylindrical bore and until said finger members biased to said extended position by said biasing means engage said opening of said cylindrical bore.

10. The probe of claim 9 wherein said coupling means comprises a pivot member pivoted for rotation about a pivot axis transverse to said radially extending recess, said finger members engaging said pivot member to selectively reciprocally rotate said pivot member about said pivot axis and said pivot member also engaging eddy current detector assembly to extend and retract said eddy current detector assembly as said pivot member is rotated by said finger members.

11. The probe of claim 10 wherein said biasing means comprises a first spring means biasing said current detector assembly radially outward from said radially extending recess, and second stronger spring means biasing said finger members radially outward, and wherein said pivot member engages said eddy current detector assembly through a lost motion connection.

12. The probe of claim 10 wherein said eddy current detector assembly comprises a housing slidable in said radially extending recess and an eddy current coil mounted on said housing, and wherein said lost motion connection comprises a slot in said carrier wider than said pivot member.

13. The probe of claim 12 wherein said finger members comprise a pair of diametrically opposed shoes and stems connected to said shoes and reciprocally slidable in opposite directions in adjacent paths, said shoes having confronting inclined surfaces forming a V in which said pivot member seats, said V converging to rotate said pivot member as said stems slide in said opposite directions upon retraction of said finger members through contact with the open end of said cylindrical bore.

14. A probe for inspecting the interior walls of a hollow metallic plug having an open end and a cylindrical bore with a radially expanded section spaced from said open end, said probe comprising:
an elongated body insertable into said cylindrical bore through said open end, and having a radially extending recess;
an eddy current assembly slidable radially in said radially extending recess; and
actuating means comprising a pivot member pivoted for rotation about a pivot axis transverse to said radially extending recess, and a linear actuator supported by said elongated body and having an actuating rod reciprocally movable axially within said elongated body, said actuating rod connected to said pivot member to selectively reciprocally rotate said pivot member which couples to said eddy current detector assembly to extend and retract said eddy current detector assembly in said radially extending recess.

15. The probe of claim 14 wherein said linear actuator comprises an electrical solenoid.

16. The probe of claim 14 wherein said pivot member couples to said eddy current detector assembly through a lost motion connection, and including spring means biasing said eddy current detector assembly radially outward in said radially extending recess.

17. The probe of 16 wherein said lost motion connection comprises a slot in said eddy current detector assembly wider than said pivot member.

18. The probe of claim 14 wherein said pivot member is pivoted intermediate first and second ends and wherein said first end is connected to said actuating rod of the linear actuator by a sliding connection, and said second end of said pivot member engages said eddy current detector assembly.

19. The probe of claim 18 wherein said second end of said pivot member is connected to said eddy current detector assembly through a lost motion connection.

20. The probe of claim 19 wherein said lost motion connection comprises a slot in said eddy current detector assembly which is wider than said second end of said pivot member.

21. The probe of claim 20 wherein said linear actuator is an electrical solenoid.

* * * * *